(12) United States Patent
Pike et al.

(10) Patent No.: US 7,592,176 B2
(45) Date of Patent: Sep. 22, 2009

(54) METHOD OF FORMING MESENCHYMAL STEM CELLS FROM EMBRYONIC STEM CELLS

(75) Inventors: J. Wesley Pike, Madison, WI (US); Nirupama K. Shevde, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/123,794

(22) Filed: May 6, 2005

(65) Prior Publication Data

US 2006/0008902 A1      Jan. 12, 2006

Related U.S. Application Data

(60) Provisional application No. 60/569,500, filed on May 7, 2004.

(51) Int. Cl.
C12N 5/00 (2006.01)
C12N 5/08 (2006.01)
A61K 48/00 (2006.01)

(52) U.S. Cl. ............ 435/373; 435/366; 424/93.21

(58) Field of Classification Search .......... None
See application file for complete search history.

(56) References Cited

U.S. PATENT DOCUMENTS

| | | | |
|---|---|---|---|
| 5,486,359 | A | 1/1996 | Caplan et al. |
| 5,843,780 | A | 12/1998 | Thomson |
| 6,863,900 | B2 | 3/2005 | Kadivala et al. |
| 2003/0021771 | A1 * | 1/2003 | Xu et al. ............ 424/93.21 |
| 2003/0036194 | A1 | 2/2003 | Xu et al. |
| 2006/0057720 | A1 | 3/2006 | Xu et al. |

FOREIGN PATENT DOCUMENTS

| | | |
|---|---|---|
| WO | WO 03/004605 A2 | 1/2003 |
| WO | WO 03/082300 A1 | 10/2003 |

OTHER PUBLICATIONS

Mesencult Basal Medium (Human) Product Information Sheet. Stem Cell Technologies, Inc. Revised Oct. 2001.*
Denning, C and H Priddle. Reproduction 126:1-11, 2003.*
Verfaillie, C et al. Hematology 369-391, 2002.*
Gepstein, L. Circ Res 91:866-876, 2002.*
Stewart, MH et al. Nature Methods 3(10):807-815, 2006.*
Ordoric, JS et al. Stem Cells 19:193-204, 2001.*
Beresford, J.N., et al., "The Effects of Dexamethasone anf 1,25-Dihydroxyvitamin D3 on Osteogenic Differentiation of Human Marrow Stromal Cells In Vitro," Archs Oral Biol. 39:941-947 (1994).
Buttery, L.D.K., "Differentiation of Osteoblasts and In Vitro Bone Formation from Murine Embryonic Stem Cells," Tissue Engineering 7:89-99 (2001).
Sottile, V., et al., "In Vitro Osteogenic Differentiation of Human ES Cells," Cloning and Stem Cells 5:149-155 (2003).
zur Nieden, N. I., et al, "In Vitro Differentiation of Embryonic Stem Cells into Mineralized Osteoblasts," Differentiation 71:18-27 (2003).
Bianco, P., et al., "Bone Marrow Stromal Stem Cells: Nature, Biology, and Potential Applications," Stem Cells 2001 19:180-192.
Bielby, R.C., et al, "In Vitro Differentiation and In Vivo Mineralization of Osteogenic Cells Derived from Human Embryonic Stem Cells," Tissue Engineering 10:1518-1525 (2004).
Bruder, S.C., et al., "Mesenchymal Stem Cells in Bone Development, Bone Repair, and Skeletal Regeneration Therapy," Journal of Cellular Biochemistry 56:283-294 (1994).
Dani, C., et al., "Differentiation of Embryonic Stem Cells into Adipocytes In Vitro," Journal of Cell Science 110:1279-1285 (1997).
DeLuca, H.F., "The Vitamin D Sysem: Receptor, Analogs and Functions," Abstract Mosbacher Kolloquium Apr. 1-3, 2004, How Nutrients Influence Gene Activity.
Dieudonne, S.C., et al., "Osteoblast differentiation of bone marrow stromal cells cultured on silica gel and sol-gel-derived titania," Biomaterials 23:3041-3051 (2002).
Minguell, J.J., et al., "Mesenchymal Stem Cells," Minireview, Exp. Biol. Med. 226:507-520 (2001).
Saravanapavan, P., et al., "Low-temperature synthesis, structure, and bioactivity of gel-derived glasses in the binary CaO-Si02 System," J. Biomed Mater Res 54:608-618 (2001).
Shamblott, M.J., et al., "Human embryonic germ cell derivatives express a broad range of developmentally distinct markers and proliferate extensively in vitro," PNAS 98:113-118 (2001).

(Continued)

*Primary Examiner*—Deborah Crouch
*Assistant Examiner*—Marcia S Noble
(74) *Attorney, Agent, or Firm*—Quarles & Brady LLP

(57) ABSTRACT

This invention relates to methods of producing a substantially homogenous population of mesenchymal stem cells derived from embryonic stem cells. Also, disclosed is a homogenous population of mesenchymal stem cells capable of further differentiating into a variety of specific cell types, characterized by various morphological factors and cell-specific markers. The compositions and methods described in this disclosure are useful for a variety of commercially important diagnostic, drug screening, and therapeutic applications.

9 Claims, 7 Drawing Sheets

OTHER PUBLICATIONS

Shevde, N.K., et al., "A potent analog of 1alpha,25-dihydroxyvitamin D3 selectively induces bone formation," PNAS 99:13487-13491 (2002).

Silva, Jr., W.A., et al., "The Profile of Gene Expression of Human Marrow Mesenchymal Stem Cells," Stem Cells 21:661-669 (2003).

Thomson, J.A., et al., "Embryonic Stem Cell Lines Derived from Human Blastocysts," Science 282:1145-1147 (1998).

Tsugawa, N., et al., "In Vitro Biological Activities of a Series of 2beta-Substituted Analogues of 1alpha,25-Dihydroxyvitamin D3," Biol. Pharm. Bull, 23:66-71 (2000).

Check, Erika, "Stem Cell Paper Corrected," Nature 447:14, p. 763 (Jun. 2007).

Chi, Kelly Rae, "Adult Stem Cell Figure Retracted," The Scientist (Jun. 2007).

* cited by examiner

Bone Nodule Formation in Osteoblasts Derived from hES Cells

Retinoic Acid treatment          1,25(OH)$_2$D$_3$ treatment

Histological Evaluation of Nodules Generated in Athymic Nude Mice

A

Large areas of cartilagenous nodules (4X)

B

Evidence of endochondral bone formation (10X)

C

Hyperthrophic chondrocytes embedded in bone (20X)

D

Cartilage with hypertrophic chondrocytes and matrix (40X)

In Vitro Bone Nodule Formation with 1,25(OH)$_2$D$_3$ or BMP Treatment

A

Control

B

BMP2

C 1,25(OH)$_2$D$_3$

D 1,25(OH)$_2$D$_3$
+ BMP

Mice from Control and Experimental Groups 1 Week following Subcutaneous Injections

Control Group

Experimental Group

Progression of Nodule Growth in Athymic Nude Mice from Week 1 to Week 8

Week 1

Week 6

Week 8

METHOD OF FORMING MESENCHYMAL STEM CELLS FROM EMBRYONIC STEM CELLS

CROSS-REFERENCE TO RELATED APPLICATIONS

This application claims the benefit of U.S. Provisional Application No. 60/569,500 filed May 7, 2004, which is incorporated herein by reference in its entirety.

STATEMENT REGARDING FEDERALLY SPONSORED RESEARCH OR DEVELOPMENT

Not applicable.

BACKGROUND OF THE INVENTION

Embryonic stem cells are pluripotent cells capable of both proliferation in cell culture as well as differentiation towards a variety of lineage restricted cell populations that exhibit multipotent properties (Odorico et al., (2001) *Stem Cells* 19:193-204). Human embryonic stem cells are thus capable of commitment and differentiation to a variety of lineage-restricted paths resulting in very specific cell types that perform unique functions. Multipotent stem cells of mesodermal origin during development give rise to bone, cartilage, tendon, muscle and fat (Minguell et al., (2001) *Exp. Biol. Med.* 226:507-520). Postnatally, these same cells are termed mesenchymal stem cells (MSCs) and can be found in relative abundance in bone marrow. Since MSCs by definition retain a self-renewing property, they can be isolated and expanded in culture. Researchers have found that intravenous injection of these cells results in the presence of long lasting precursor cells in various tissues capable of restoring the levels of specific stem cell precursors depleted as a result of aging or disease. As such, MSCs represent a potential mechanism for gene therapy (Bianco et al., (2001) *Stem Cells* 19:180-192). More importantly, it has been found that implantation of these cells in various animal model systems leads to the differentiation of these cells at localized sites and the subsequent regeneration of tissues such as muscle, tendon, cartilage and bone.

One source of multipotent stem cells that can be expanded in culture and utilized locally for potential bone regeneration, bone healing and fracture repair is bone marrow-derived MSCs (Bruder et al., (1994) *J. Cell Biochem.* 56:283-294). Studies of this nature using bone marrow-derived MSCs have been carried out in animal models but have not been conducted in humans perhaps because of some inherent limitations in the use of MSCs. For example, despite the capacity to expand these cells in vitro, MSCs represent a rare subpopulation of cells found in the bone marrow. Thus, the isolation of bone-derived MSCs requires extensive purification.

Other limitations encountered when using this population of MSCs is that they are significantly heterogeneous. For example, there is extensive variability in cell expansion capabilities, some exhibiting the ability to undergo numerous cell doublings whereas others have a much reduced capacity (Minguell et al., (2001)). Expanded MSC populations can also exhibit features of senescence and apoptosis. Other limitations of these cells originate from the variability in the human sources from which they are derived. For example, MSC populations derived from bone marrow populations are influenced by a variety of factors such as sex, age and physiological condition of the donor.

An alternative source of MSCs with perhaps less inherent limitations is believed to be embryonic stem cells (ES cells). ES cells are now routinely prepared from a variety of species including rodents, primates and man. Techniques for isolating stable cultures of human ES cells have recently been described by Thomson et al., in U.S. Pat. No. 5,843,780 and J. Thomson et al., (1998) *Science* 282:1145-1147, both of which are hereby incorporated by reference in their entirety.

Generally, ES cells are highly homogeneous, exhibit the capacity for self-renewal, and have the ability to differentiate into any functional cell in the body. This self-renewal property can lead under appropriate conditions to a long-term proliferating capability with the potential for unlimited expansion in cell culture. Furthermore, it is understood, that if human ES cells are allowed to differentiate in an undirected fashion, a heterogeneous population of cells is obtained expressing markers for a plurality of different tissue types (WO 01/51616; Shamblott et al., (2001) *Proc. Natl. Acad. Sci. U.S.A.* 98:113). These features make these cells a unique homogeneous starting population for the production of cells having therapeutic utility.

There have been efforts by researchers in the field to use mouse ES cells to expand and differentiate into numerous cell lineages and restore depleted cell populations in rodent models. Specifically, mouse ES cells have been expanded and differentiated via the formation of embryoid bodies into cells capable of expressing bone osteoblast marker genes and forming mineralized bone in vitro (Dani et al., (1997) *J. Cell Sci.* 110:1279-85).

Also, others have reported differentiation of bone marrow-derived human mesenchymal stem cells (hMSC) into cells of more than one connective tissue type, such as bone, cartilage, tendon, ligament, and dermis (see U.S. Pat. No. 5,486,359). Other systems have been proposed for regeneration and augmentation of bone using mesenchymal stem cells, combined with a ceramic material or resorbable biopolymer as disclosed in International patent publication WO 97/40137.

Furthermore, pluripotent stem cell populations have been isolated from human blastocysts such that 30% of the cells are derived from mesenchymal cells and can be identified by expression of osteonectin or osteocalcin (see U.S. Published Application No. 20030036194). To our knowledge, however, these ES cell-derived populations are not homogenous MSC populations and have not effectively enhanced bone formation in vivo. Accordingly, a significant challenge in using human ES cells for therapeutic purposes, or for studying particular cell types in vitro, has been to obtain cell populations that include a substantial subpopulation that is relatively uniform in characteristics.

It is noted that none of the above reviewed publications teach or suggest a method for deriving a substantially homogenous population of mesenchymal stem cells from human ES cells. Also, it is unclear whether any of the cell preparations exemplified in the art can be produced in sufficient quantities for mass marketing as a therapeutic composition for use in bone repair. Therefore, to realize the potential of human embryonic stem cells in managing human health and disease, it would be useful to develop novel methods for efficiently isolating a substantially homogenous population of mesenchymal stem cells from human ES cells for production of therapeutically important tissue types.

BRIEF SUMMARY OF THE INVENTION

The present invention is broadly summarized as methods of producing a substantially homogenous population of mesenchymal stem cells derived from embryonic stem cells. The population of mesenchymal stem cells is capable of further differentiating into a variety of specific cell types, characterized by various morphological factors and cell-specific markers.

Specifically, in one aspect, the invention provides a simplified method for selectively promoting the formation of a substantially homogenous population of mesenchymal stem cells derived from embryonic stem cells. This is done by culturing embryonic stem cells under conditions conducive for the formation of embryoid bodies. The embryoid bodies are propagated in mesenchyme-specific medium and digested to form mesodermal cells. The mesodermal cells are further cultured in mesenchyme-specific medium to form a substantially homogenous population of mesenchymal stem cells.

In a related aspect, the substantially homogenous population of mesenchymal stem cells can be further propagated in the presence of an effective amount of $1.25(OH)_2D_3$ to produce a subpopulation of bone-precursor cells including pre-osteoblasts and osteoblasts.

In this aspect, mesenchymal stem cells having osteoblastic potential are further cultured in the presence of effective amounts of $1.25(OH)_2D_3$, dexamethasone, retinoic acid, or combinations thereof, followed by the addition of effective amounts of ascorbic acid and β-glycerophosphate to promote differentiation of the MSCs into pre-osteoblasts and osteoblasts.

In yet another aspect the invention provides a homogenous population of mesenchymal stem cells derived from embryonic stem cells.

In this aspect, the homogenous population is composed of no less than 60% and preferably 90% mesenchymal stem cells exhibiting spindle shaped morphology.

In this aspect, the homogenous cell population may be further cultured in the presence of an effective amount of $1.25(OH)_2D_3$ to selectively promote the formation of bone precursor cells including pre-osteoblasts and osteoblasts.

In this aspect, the pre-osteoblasts and osteoblasts secrete matrix proteins and undergo mineralization.

In this aspect, the pre-osteoblasts or osteoblasts are characterized by the expression of early transcription factors, such as, but not limited to Cbfa-1, Msx2, and D1x5.

Also, in this aspect, the pre-osteoblasts or osteoblasts are characterized by the expression of osteoblast specific genes, such as, but not limited to osteopontin, osteonectin, and osteocalcin.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used.

Other objects, advantages and features of the present invention will become apparent from the following specification taken in conjunction with the accompanying drawings.

DETAILED DESCRIPTION OF THE INVENTION

Figure 1:
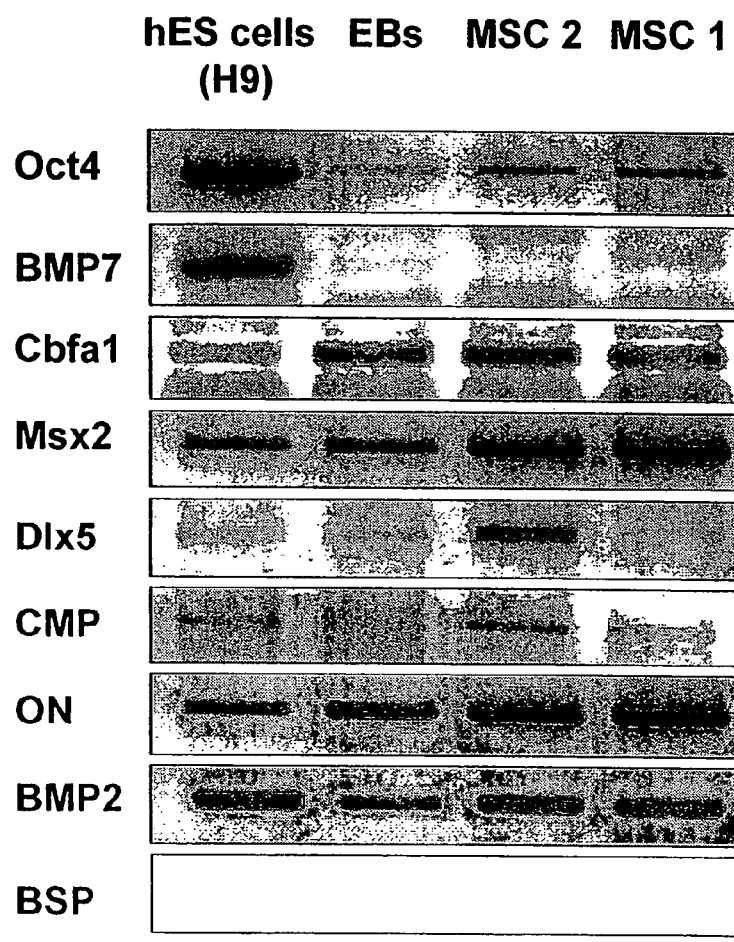
FIG. 1 depicts RT-PCR analysis of RNA isolated from hES cells, digested EBs and cells cultured into two separate media and sera (MSCs 1 and MSCs 2).

This invention is based on the discovery that a substantially homogenous population of mesenchymal stem cells may be obtained derived from embryonic stem cells. The population of mesenchymal stem cells is capable of further differentiating into a variety of specific cell types, characterized by various morphological factors and cell-specific markers.

In a broad sense, the invention provides a simplified method for selectively promoting the formation of a substantially homogenous population of mesenchymal stem cells derived from embryonic stem cells. This is done by culturing embryonic stem cells under conditions conducive for the formation of embryoid bodies. The embryoid bodies are propagated in mesenchyme-specific medium and digested to form mesodermal cells. The mesodermal cells are further cultured in mesenchyme-specific medium to form a substantially homogenous population of mesenchymal stem cells.

In a related embodiment, the substantially homogenous population of mesenchymal stem cells can be further propagated in the presence of an effective amount of $1.25(OH)_2D_3$ to produce a subpopulation of bone-precursor cells including pre-osteoblasts and osteoblasts. These cells are competent to mineralize and thus form bone.

In a related embodiment, the method can be further simplified by directly treating embryoid bodies derived from ES cells, or mesodermal cells with an effective amount of $1.25(OH)_2D_3$ to facilitate formation of mesenchymal stem cells. Direct treatment of embryoid bodies with $1.25(OH)_2D_3$ permits mesenchymal stem cell cultures to be created that are relatively homogenous, having in excess of 90% of the cells being mesenchymal stem cells, in a relatively rapid and convenient protocol. Normally it takes about 10 to 12 days to culture human ES cells into embryoid bodies. Then, to go from embryoid bodies to a homogenous human MSC culture using this new method takes only a total time period of less than 10 days, and typically 6 to 8 days. When the efficiency of this process is combined with the process to induce the MSCs to become bone-forming osteoblasts described below (which takes 7 to 14 days), it is possible to go from human ES cells to bone-forming osteoblasts in less than 34 days, and in as few as 23 days, of culture to achieve both differentiation and mineralization.

In a specific embodiment, the invention provides a method for producing a substantially homogenous population of pre-osteoblast and osteoblast cells. Human ES cells are cultured into embryoid bodies which are then cultured in the presence of a mesenchyme-specific medium that favors the optimal propagation of mesenchymal stem cells as described above to form a homogenous population of MSCs. The MSC population is further cultured in osteogenic medium, where effective amounts of osteoblast differentiation agents are introduced into the medium in a sequence-specific manner. This is performed by initially introducing $1.25(OH)_2D_3$, dexamethasone, retinoic acid, or combinations thereof, to the osteogenic culture medium followed by the addition of ascorbic acid and β-glycerophosphate. This promotes differentiation of the MSCs into a substantially homogenous population of cells expressing gene markers and exhibiting cell morphology characteristic of bone-forming cells. Accordingly, the remarkable uniformity and functional properties of the cells produced by the methods of the invention make them valuable (1) for preparing and characterizing hMSCs involved in the turnover and repair of bone; (2) for developing new therapeutic models; and (3) as a tool for studying mesenchymal tissues in vitro.

In another embodiment, the invention provides a substantially homogenous population of mesenchymal stem cells derived from human embryonic stem cells. The homogenous population is composed of no less than 60% and preferably 90% mesenchymal stem cells exhibiting spindle shaped morphology. The MSC population may be further cultured in the presence of an effective amount of $1.25(OH)_2D_3$ to selectively promote the formation of bone precursor cells, including pre-osteoblasts and osteoblasts. The pre-osteoblasts and osteoblasts secrete matrix proteins and undergo mineralization. Also, the pre-osteoblasts or osteoblasts are characterized by the expression of early transcription factors, such as, but not limited to Cbfa-1, Msx2, and D1x5. These cells are characterized by the expression of osteoblast specific genes, such as, but not limited to osteopontin, osteonectin, and osteocalcin.

In general, as used herein the term "mesenchymal stem cells" or "MSCs" refers to a population of cells derived from embryonic stem cells. MSCs directly originate from the mesoderm and are either partially differentiated cells or proliferative precursor cells committed to form cells of a mesenchymal tissue (such as bone derived from osteoblast cells), dental tissue, cartilage, tendon, bone marrow stroma, or muscle. Mesenchymal stem cells are included in the term, as are differentiated (post-mitotic) cells and more committed replication-competent cells, such as bone precursor cells.

MSCs can be induced to proliferate and differentiate in different ways. MSCs can be cultured on a substrate coated with an appropriate material conducive to growth of the desired cell phenotype, or MSCs can be cultured in a medium containing a variety of components to induce growth. For example, in accordance with the invention, MSCs may be cultured in mesenchyme-specific medium. The term "mesenchyme-specific medium" as used herein refers to a culture medium containing MesenCult™ Basal Medium and 10% FBS for human mesenchymal stem cells. This medium which is made of McCoy's base, specifically McCoy's 5A medium (modified) supplemented with 2.0 mM L-Glutamine is essentially used for the expansion and differentiation of human mesenchymal stem cells. Although all of the components of the MesenCult™ Basal Medium are not disclosed by the manufacturer, applicants believe that the following is a non-limiting list of suitable components: non-essential amino acids, ribonucleosides, deoxyribonucleosides, L-glutamine, sodium bicarbonate, and Vitamin B12. Accordingly, it is envisioned that other media, besides McCoy's base, containing the above-mentioned components can be utilized to facilitate MSC differentiation. To verify that other mesenchyme-specific media will work as well, we have also tested alpha MEM medium (Earl's) with glutamine and nucleosides added, and it worked as well as the MesenCult medium. Another useful mesenchyme-specific medium is DMEM with glucose and glutamine, although it may lead to a slightly decreased yield of embryoid bodies. Characterized or defined serum products from various manufacturers can be used in place of the pre-tested serum in the media below as well.

Furthermore, to optimize the expansion of human mesenchymal cells, Fetal Bovine Serum (FBS) pre-tested for optimal growth of hMSCs (available through Stem Cell Technologies, Vancouver, Canada) may be added to the MesenCult™ Basal Medium. Although the components of FBS are not disclosed by the manufacturer, applicants believe that the following is a non-limiting list of suitable components that may influence the growth of MSCs: transferrins, cytokines/growth factors such as insulin growth factors (IGFs), basic fibroblast growth factor (bFGF), stem cell factor (SCF), bone morphogenic proteins (BMPs) including and not limited to BMP 2, 4, 7, 9 and 12. These components have been pretested and selected for their ability to optimally initiate and maintain human mesenchymal cell proliferation.

It is envisioned that Matrigel™, laminin, collagen (especially collagen type I), glycosaminoglycans, osteocalcin, and osteonectin may all be suitable as an extracellular matrix, by themselves or in various combinations. Also potentially suitable for growing osteoblast lineage cells are gel-derived glasses, silica gels, and sol-gel-derived titania (Saravanapavan et al., (2001) *J. Biomed Mater. Res.* 54:608; Dieudonne et al., (2002) *Biomaterials* 34:3041.

Furthermore, the MSCs produced by the methods of this invention may be characterized according to a number of phenotypic criteria. For example, relatively undifferentiated mesenchymal cells can be recognized by their characteristic mononuclear ovoid, stellate shape or spindle shape, with a round to oval nucleus. The oval elongate nuclei typically have prominent nucleoli and a mix of hetero- and euchromatin. These cells have little cytoplasm but many thin processes that appear to extend from the nucleus. It is believed that MSCs will typically stain for one, two, three or more of the following markers: CD106 (VCAM), CD166 (ALCAM), CD29, CD44, GATA-4, and alkaline phosphatase, while being negative for hematopoietic lineage cell markers (CD14 or CD45). MSCs may also express STRO-1 as a marker.

Also, as used herein, the term "differentiate" or "differentiated" refers to a cell that has progressed further down a developmental pathway or lineage than the cell it is being compared with. Pluripotent embryonic stem cells can differentiate to lineage-restricted precursor cells (such as mesenchymal stem cells), which in turn can differentiate into other types of precursor cells further down the pathway (such as pre-osteoblast or osteoblasts), and then to an end-stage differentiated cell, which plays a characteristic role in a certain tissue type (such as bone), and may or may not retain the capacity to proliferate further. As used herein the term bone precursor cell refers to "pre-osteoblast" and "osteoblast" cells. These bone precursor cells are more mature cells that are further along the hMSC lineage. These cells are characterized by the expression of early transcription factors, such as, but not limited to, Cbfa-1, Msx2, and D1x5, as well as the expression of osteoblast-specific genes such as, but not limited to, osteopontin, osteonectin, and osteocalcin.

As used herein, the term "osteoblast differentiation agent" refers to one of a collection of compounds that are used in culture systems of this invention to produce differentiated cells of the mesenchymal lineage (including pre-osteoblasts, osteoblasts and terminally differentiated cells). No limitation is intended to be placed on the mode of action of the osteoblast differentiation agents. For example, the agent may facilitate the differentiation process by inducing or assisting a change in phenotype, promoting growth of cells with a particular phenotype or retarding the growth of others, or acting in concert with other agents through unknown mechanisms.

General examples of suitable osteoblast differentiation agents may include but are not limited to one or more of the following general compounds: (1) bone morphogenic proteins, exemplified by BMP-2, BMP-3, BMP-4, BMP-6 and BMP-7; (2) TGF-β, exemplified by TGF-β1, TGF-β2, and TGF-β3 and their analogs, and other members of the TGF-β superfamily that bind a TGF-β receptor; and (3) ligands for the Vitamin D receptor. Exemplary is 1.25-dihydroxyvitamin $D_3$. Other known vitamin $D_3$ analogs may also be suitable (see, for example, Tsugawa et al., (2000) *Biol. Pharm. Bull.* 23:66).

Most preferably, however, the osteoblast differentiation agents of the invention include the following non-limiting compounds and their respective concentration ranges: 1.25 $(OH)_2D_3$ ($10^{-9}$ to $10^{-7}M$), dexamethasone ($10^{-9}$ to $10^{-7}M$), retinoic acid ($10^{-9}$ to $10^{-5}M$), or combinations thereof, in addition to ascorbic acid (50 to 100 μg/ml) and β-glycerophosphate (1 to 10 mM). These agents are supplied to the mesenchyme-specific culture medium in a sequence-specific manner, by adding an effective amount of $1.25(OH)_2D_3$, dexamethasone, retinoic acid or combinations thereof to the medium followed by the addition of ascorbic acid and β-glycerophosphate to promote differentiation of the MSCs into a substantially homogenous population of bone precursor cells. These organic compounds are generally used to mimic local bone microenvironments. Applicants note that with the knowledge of the specific concentrations of osteoblast differentiation agents provided in the example below, those skilled in the art would be able to readily determine what would constitute an "effective amount" or optimal concentration range for osteoblast differentiation agents.

Furthermore, it is recognized that antibodies specific to the receptors of any of these factors are functionally equivalent ligands that can be used in place of (or in addition to) the factors listed. Other additives that may be used include: other morphogens, such as a fibroblast growth factor like basic FGF; a glucocorticoid; dexamethasone, or other small-molecule osteoblast maturation factor; ascorbic acid (or an analog thereof, such as ascorbic acid-2-phosphate), which is a cofactor for proline hydroxylation that occurs during the course of collagen synthesis; β-glycerophosphate, or other substrate for alkaline phosphatase during the process of mineralization It is understood by the skilled artisan that bone precursor cells will typically have at least one characteristic and typically at least three or five of the following characteristics: 1) density between ~1.050 and ~1.090 g $cm^{-3}$; 2) positive for osteonectin (positive in osteoblasts and precursors) and related osteoblast transcription factors described below; 3) positive for osteocalcin (specific for mature osteoblasts); 4) a cell diameter of ~8 to ~70 micron; 5) cuboidal shape; 6) upregulated production of alkaline phosphatase, especially in response to presence of BMP; 7) positive for type I collagen (procollagen) or for vimentin; 8) positive for other osteoblast-specific markers, such as BMP receptors, PTH receptors, or CD105 (endoglin); 9) evidence of ability to mineralize the external surroundings, or synthesize calcium-containing extracellular matrix.

To determine the function of the homogenous population of bone precursor cells, expression of tissue-specific gene products may be detected at the mRNA level by Northern blot analysis, dot-blot hybridization analysis, or by reverse transcriptase initiated polymerase chain reaction (RT-PCR) using sequence-specific primers in standard amplification methods. See for example: U.S. Pat. No. 5,843,780 for details of general technique, and International Patent Publication WO 99/39724 for osteoblast-specific PCR primers. Sequence data for other markers listed in this disclosure can be obtained from public databases such as GenBank (URL www.ncbi.nlm.nih.gov:80/entrez). Expression at the mRNA level is generally "detectable" according to any one of the assays described in this disclosure providing the performance of the assay on cell samples results in clearly discernable hybridization or amplification product. Expression of tissue-specific markers as detected at the protein or mRNA level is considered positive if the level is at least 2-fold, and preferably more than 10- or 50-fold above that of a control cell, such as an undifferentiated MSC population or other unrelated cell type.

It is understood that adjustment of culture and cell separation conditions to include, eliminate, or substitute particular components is a matter of routine optimization normally expected for inventions of this kind, and does not depart from the spirit of the claimed invention.

The following examples are provided as further non-limiting illustrations of particular embodiments of the invention.

EXAMPLES

Unless explicitly indicated otherwise, the methods of this invention can be brought to bear without restriction on any type of progenitor cell, suitably human ES cell lines capable of differentiating into mesenchymal stem cells.

Digestion of ES Cells to Culture Embryoid Bodies

In this embodiment human ES cells, such as the H9 cell line, were obtained from the WiCell Research Institute (Madison, Wis.). Applicants note that the H9 stem cell line is registered with the NIH Human Embryonic Stem Cell Registry making it eligible for federal funding. It is encompassed that other human ES cells could be used in practicing the method of the invention, such as for example the H1 and H11 cell line. The human ES cells were cultured and maintained in 6-well plates (Nunc/Costar, Catalog No. 07-200-83) over a layer of $7.5 \times 10^4$ MEFs. Specifically, the H9 cell line was cultured on mouse embryonic fibroblastic (MEFs) layers in 80% DMEM-F12 medium supplemented with 20% KO serum replacer (Invitrogen, Carlsbad, Calif.) to ensure that they continued to proliferate but did not undergo differentiation. In order to initiate the process of MSC production, ES cells were allowed to undergo the process of natural progression and differentiation in vitro via the formation of embryoid bodies (EBs) (Odorico, et al., (2201) Stem Cells 19:193-204). Also, encompassed within the scope of this invention are alternative technologies to effectively culture human stem cells in a feeder free manner without the need to form embryoid bodies Embryoid bodies are routinely cultured in pre-coated T-25 flasks. The pre-coating of flasks with poly-HEME solution is essential to minimize attachment and differentiation of the EBs. Alternatively, attachment and differentiation of EBs can be minimized by placing the flasks on an orbital shaker able to fit into an incubator (e.g., Orbitron Rotator II, Model #

260250 by Boekel Scientific, PA). The T25 flasks (Falcon/Becton Dickinson, non-treated polystyrene culture surface Catalog No. 353009) or Greiner Bio-One, T25 flasks with filter caps (ISC Bioexpress Catalog No. T-3002-2) were pre-coated with poly-HEME (poly (2-hydroxyethyl methacrylate)- Sigma, Catalog No. P3932). The 2% poly-HEME solution was prepared by dissolving 1 gram of poly-HEME in 50 ml 1:1 ethanol: acetone (25 mls each). Poly-HEME dissolves more rapidly when shaken at 37° C. Poly-HEME solution (2 ml) was added to each T25 flask in a sterile hood. To ensure complete coverage of the entire culturing surface, the flask was tipped on all sides, (5 minutes for each side). The solution was then aspirated and the flasks were allowed to dry in the hood (biological safety cabinet) for 30 to 60 minutes.

In order to prepare EBs from the hES cells, medium from each well was gently aspirated by using vacuum suction, and 1 ml of freshly made dispase solution (0.5 mg/ml) was added to each well. Dispase solution was made by dissolving dispase (Invitrogen, Catalog No. 17104-019) in the medium (DMEM/F12—Invitrogen, Catalog No. 11330-032 or MesenCult™, Stem Cell Technologies, Catalog No. 05401) without serum. Cells were then returned to the incubator at 37° C. for 30 minutes. Colonies on the culture plates were examined under the microscope and the cells were deemed ready for transfer if more than 50% of the colonies were detached and the others were partially detached or showed rounded or rolled edges. All the wells were gently rinsed to detach the loosely attached colonies and if necessary, the attached colonies were gently scraped with the tip of a 5 ml glass pipette (Fisher Scientific, Catalog No. 13-678-27E). If fewer than 50% of the colonies were detached, the incubation time was extended for another 15-30 minutes (but never more than 1 hour).

All the colonies/cell clumps were transferred along with the dispase solution to 15 ml conical tubes (1 tube per 6 well plate) and were centrifuged at 500 rpm for 8 minutes rather than allowing the colonies to settle by gravity. Dispase solution was aspirated away and the cells were resuspended in 10 ml mesenchyme-specific medium in each tube. Mesenchyme-specific medium includes MesenCult™ medium with 10% FBS pre-tested for hMSCs, (Stem Cell Technologies, Catalog No. 06472). The pre-coated T25 flasks were rinsed/washed twice (5 ml each) with mesenchyme-specific medium just prior to resuspending the cells into the flasks. To each flask was added 8 ml of mesenchyme-specific medium followed by 2 ml of cell suspension (after gentle but thorough mixing), yielding a total of 10 flasks from 2-6 well plates. Other mesenchyme-specific media tested include alpha MEM medium (Earl's) with glutamine and nucleosides added and well as DMEM medium with glucose and glutamine added.

Maintenance of Embryoid Bodies

All the flasks were then returned to the incubator. The development of embryoid bodies (EBs) was monitored every day by microscopic examination. A complete medium change was carried out for all flasks every 2 days. If an orbital shaker was unavailable, in order to prevent the settling and attachment of the EBs to the bottom/edges of the flask, the flasks were shaken and the medium was agitated by tapping on the sides of the flasks at least 2-3 times a day. Most EBs exhibit a tendency to attach to the flask typically after 7-8 days in culture. It is almost impossible to prevent the attachment of EBs but it can be minimized with the above procedure. If it was found that a certain flask contained more than 10 attached EBs at the bottom/edges, the EBs from that flask were transferred to a new pre-coated flask. Total incubation time for EBs was between 10 to 12 days.

Digestion of Embryoid Bodies

After the EBs had been cultured for 10 to 12 days, microscopic examination revealed the presence of 40 or more EBs of various sizes and shapes in each flask. At this point, all the EBs in each flask along with the medium (~10 ml per flask) were collected in 15 ml conical tubes. All 10 ml tubes were centrifuged at 500 rpm for 8 minutes. The supernatant was gently aspirated and EBs were resuspended in 2 mls of 0.05% Trypsin/EDTA (Invitrogen, Catalog No. 25300-054) and 2% chick serum for 1 hour in the 37° C. water bath. In order to facilitate their optimal digestion, EBs were resuspended by gentle pipetting every 15-20 minutes for 1 hour using 10 ml glass pipettes (Fisher Scientific, Catalog No. 13-678-27F).

Following a 1 hour digestion of EBs, 5 ml of the mesenchyme-specific medium was added to each tube and the tubes were centrifuged at 500 rpm for 8-10 minutes. The supernatant was aspirated and another 5 mls of mesenchyme-specific medium was added. The cells were resuspended thoroughly and using a 10 cc syringe (BD, Catalog No. 309604) the cells were gently passed through a 23 gauge needle (BD, Catalog No. 305124) in order to break up the partially digested or undigested EBs. The entire cell suspension was then passed through a 70 micron cell strainer (Falcon/BD, Catalog No. 352350) to eliminate the debris.

Cells were then counted and cell viability was assessed using the trypan blue dye exclusion technique (see Freshney, R. I., (1994) *Culture of Animal Cells: A Manual of Basic Technique.* 3rd Ed. Wiley-Liss. New York. USA). This technique is a conventional cell viability assay which measures the percentage of cells in a cell suspension that are viable. This is generally accomplished by a dye exclusion stain, where cells with an intact membrane are able to exclude the dye while cells without an intact membrane take up the coloring agent. The dye used for exclusion stain is usually trypan blue but erythrosin and naphthalene black are also suitable dyes. The cell number should typically be in the range of 2 to $8 \times 10^6$ cells (total) depending upon the quality and the size of the EBs.

Culturing Cells of the Mesodermal Origin

After determining the total cell number, the cells were cultured on 6 well plates at a confluency of $1 \times 10^5$ or $5 \times 10^5$ cells per ml per well in either mesenchyme-specific medium or another medium containing 80% MesenCult™ medium, 10% Mesenchymal Stem Cell Stimulatory Supplements (MSCSS) (Stem Cell Technologies, Catalog No. 05402) and 10% pre-tested FBS for hMSCs. Alternatively, since MSCSS is largely composed of serum, it is envisioned that 10% MSCSS and 10% FBS could be simply substituted with 20% FBS. It is known that properties of early MSCs include spindle shaped morphology, ability to sustain high proliferative capacity and the expression of a number of genetic markers described herein. Microscopic examination of the wells revealed two distinct sub-populations of cells. One cell type was comprised of long and slender, spindle shaped cells and the other type was polygonal with several nuclei at the center. When the cells in the wells reached ~80% confluency, the cells were trypsinized using standard cell culture techniques and plated in 100 mm tissue culture dishes. Typically cells collected from 2 to 3 wells of the 6 well plates can be combined and cultured in a single 100 mm tissue culture dish (Midwest Scientific, Catalog No. TP93100).

Culture And Propagation Of Both Pre-Mesenchymal And Mesenchymal Stem Cells

To select for a population that is committed to the mesenchymal lineage, cells obtained by the above process were first cultured to near confluency in mesenchyme-specific medium. Cells were then split, transferred to new 100 mm dishes and cultured in either mesenchyme-specific medium or 80% MesenCult™ medium, 10% MSCSS and 10% pre-tested FBS for hMSCs for 3 additional passages. Microscopic examination of the cells revealed that ~80% of this population exhibited a spindle shaped mesenchymal stem cell morphology. Applicants note that in repeated experiments, several of these passages grown in 100 mm dishes were processed using standard cell culture techniques and frozen. Also, several vials of these cells were cryopreserved and stored under liquid nitrogen as a source of human MSCs.

Applicants note that with respect to the mechanism of action, it is not known whether the culture conditions utilized in the invention induce human ES cells to adopt an osteoblast phenotype, whether they promote outgrowth of cells of this type, or if they inhibit growth of other cell types—indeed, it is quite possible that several of these mechanisms work in concert to enrich for cells of the desired type. Of course, the mechanism responsible for causing enrichment for cells of the osteoblast lineage is of interest, but it is not necessary to understand the mechanism in order to practice the invention.

Culture And Propagation Of Pre-Osteoblasts And Osteoblasts

To assess the osteoblastic potential of the cell population exhibiting spindle shaped mesenchymal stem cell morphology, cells were plated in 6-well plates at $5 \times 10^5$ cells per well per ml of 90% DMEM/F12 and 10% FBS for human osteogenic cells (Stem Cell Technologies, Catalog No. 06474). Cells were generally cultured for a period of 18 to 21 days, with a complete medium change at every 2 to 3 day interval; however, cultures may be continued for a longer time period if larger bone nodules are desired.

In a preferred embodiment of the invention, the cells were initially cultured for 18 to 21 days in the presence of osteoblast differentiation agents to promote MSC differentiation into osteoblasts. The cells were preconditioned with "hormone" for 8 to 12 days with a media change every 2 to 3 days. The term "hormone" as used herein refers to $1.25(OH)_2D_3$ alone ($10^{-10}$ to $10^{-7}$M) or accompanied by dexamethasone ($10^{-9}$ to $10^{-7}$M) or retinoic acid ($10^{-9}$ to $10^{-5}$M), or both. After the cells were suitably preconditioned with hormone, then "bone mineralizing factor(s)" were introduced into the culture every 2 to 3 days for at least an additional 8 days or until osteoblast formation was observed. The term "bone mineralizing factor" as used herein refers to ascorbic acid (50 to 100 µg/ml), β-glycerophosphate (1 to 10 mM) or both.

Most preferably, the mesenchymal stem cells in culture were consecutively treated with "hormone" to precondition the cells every 2 to 3 days for the first 9 days with a dose of $1.25(OH)_2D_3$ at $1 \times 10^{-8}$M, dexamethasone at $1 \times 10^{-7}$M, and retinoic acid at $1 \times 10^{-7}$M. These initial hormone treatments were followed by 4 consecutive treatments every 2 to 3 days with a dose of ascorbic acid (50 µg/ml) and β-glycerophosphate (10 mM) to promote differentiation of the MSCs into osteoblasts. These compounds were used to mimic local bone microenvironments. The osteoblast phenotype and the functionality of the osteoblast population were then assessed as described below.

It is noted that although it may be possible to promote osteoblast formation using various concentrations of hormone alone, bone mineralizing factor(s) alone, or a combination of hormone and bone mineralizing factor(s), applicants have found that the above described-combination of hormone followed by bone mineralizing factors provides the most efficient manner of differentiating stem cells into osteoblastic bone nodules.

Furthermore, in addition to vitamin $D_3$, a number of highly potent and highly efficacious analogs and structural mimics of $1.25(OH)_2D_3$ have been recently developed. (See Shevde et al., (2002) *PNAS* 99:13487-13491.) It is envisioned that these $1.25(OH)_2D_3$ analogs may be used as a substitute or in addition to the active metabolite of vitamin $D_3$.

Simplified Culture and Propagation of Mesenchymal Stem Cells

In addition to the above-described method for producing a homogenous population of mesenchymal stem cells from embryonic stem cells, applicants developed a more streamlined and efficient alternative procedure to produce MSCs. This alternative approach was performed by culturing ES cells in 6 well plates on mouse feeder layers in 80% DMEM-F12 medium supplemented with 20% KO serum replacer. The medium was gently aspirated from all wells and 0.5 mg/ml of dispase (in DMEM/F12 or MesenCult™ without serum) at 1 ml per well was added to each well. The cells were returned to the incubator and checked after 20 minutes. If more that 50% of the ES cell colonies were detached or show "rolled edges" the cells were gently pipetted off each well and transferred to a 15 ml conical tube. The cells were allowed to settle at the bottom by gravity for 3 minutes and then gently spun at 1000 rpm for 1 minute. The dispase was aspirated and the cells were washed once with suitable medium, such as mesenchyme-specific medium which includes MesenCult™ medium with 10% FBS pre-tested for hMSCs. The cells were then resupended in 8-10 mls of mesenchyme-specific medium and transferred to T-25 flasks that were previously coated with poly-HEME solution, which prevents attachment of the EBs to the bottom of the flask and therefore prevents differentiation of the cells. In addition to coating the flasks with poly-HEME, the flasks containing the cells were placed on a shaker platform as described above and allowed to rock for the entire duration of EB development. The medium was changed approximately every 2 days for 10 to 14 days while the EBs were allowed to develop. After 10 to 14 days the EBs were digested and replated to obtain a population of cells that have a predominantly mesodermal character. This was done by using the mesenchyme-specific medium and serum that fosters the propagation of mesenchymal stem cells. This was a mixed population of 3 to 4 cell types, which have the potential to form under suitable conditions chondrocytes, adipocytes, and bone precursor cells. After 2 days in culture, $1.25(OH)_2D_3$ at $10^{-8}$M was added to the cells to promote formation of bone precursor cells.

After 2-4 days of culture in the presence of $1.25(OH)_2D_3$, a complete change of medium was done and a second dose of $1.25(OH)_2D_3$ was added at $10^{-8}$M to the medium. It is noted that although BMP-2 can be used in addition to or as a substitute for $1.25(OH)_2D_3$, BMP-2 did not work as well as $1.25(OH)_2D_3$.

After another 2-4 days of culture, along with a complete change of culture medium, a first dose of mineralizing compounds (ascorbic acid and β glycerol-phosphate) was added to the cells. This treatment of the cells with mineralizing compounds was repeated after 2-4 days of culture. The treated cells were stained to detect bone formation following another 3 to 5 days of culture using the von Kossa staining technique.

In yet another embodiment, it is envisioned that a substantially homogeneous population of mesenchymal stem cells may be selectively formed by treating embryoid bodies derived from ES cells directly with an effective amount of $1.25(OH)_2D_3$. In these experiments, EBs were allowed to form as above. As indicated earlier, the EBs remained in culture for up to ten to twelve days. At day 6 and day 9, the EBs were treated with an effective dose of $1.25(OH)_2D_3$ along with a complete change of medium. The EBs were then digested and cultured as described above.

These simplified procedures provide researchers the ability to produce a homogenous population of MSCs at a faster rate by treating cells with 1.25(OH)$_2$ D$_3$ at an earlier stage in the process of making MSCs and eliminating 1-2 weeks off of the time it takes to produce such cells. The time period to go from embryoid bodies to a culture which is in excess of 90% human mesenchymal stem cells was cut down to less than 10 days and to as little as 6 days. The culturing of embryoid bodies from human ES cells takes usually 10 to 12 days. When these two time periods are combined with the osteoblast culture techniques described above, under which cells can be cultured to go from MSCs to bone-forming osteoblasts in 7 to 14 days, the total time required to progress from human ES cells to differentiated bone-forming cells is down to 23 to 34 days. These simplified methods can create a continuous source of relatively pure mesenchymal stem cell populations with a high proliferative potential and of bone-forming osteoblasts in a relatively short time period. Other established sources of these cell types are human bone marrow donors, which restricts the amount and availability of donated materials. Furthermore, human bone marrow contains a very small percent of mesenchymal stem cells and the age of the donors affects the proliferative potential of these cells. In growing cells for transplantation purposes, it is well known that time is of the essence, thus, the methods described herein improve the time required to obtain MSCs resulting in the preservation of life.

Determining the Functionality of the Osteoblasts

It is generally understood that a variety of factors are known to facilitate the differentiation of hES cell derived mesenchymal stem cells towards the osteoblast phenotype. These include the osteogenic bone morphogenic proteins such as BMP-4 and compounds regulating this factor including the retinoic acid, glucocorticoids, TGFβ1, interleukin 6, leptin, and 1.25(OH)$_2$D$_3$. The molecular actions of these steroid hormones, growth factors and peptide hormones are mediated by a series of transcription factors that are expressed in a timely fashion as the MSCs undergo lineage progression. Several of these osteoblast specific transcription factors include the early factors Cbfa1, D1x5, and Msx2 and the expression of osteoblast-specific genes such as osteopontin (OPN), osteonectin and osteocalcin as seen in the most mature cell types, (see Silva, et al., (2003) *Stem Cells* 21:661-9.)

As used herein, the term "Cbfa-1" refers to the Cbfa-1 transcription factor which appears to be an activator of the bone-specific protein, osteocalcin and is able to regulate the synthesis of extracellular matrix at the level of the single osteoblast. (Ducy, P. et al., (1997) *Cell* 89:747-754.

As used herein, the terms "D1x5" and "Msx2" refer to homeodomain proteins which transcriptionally regulate osteoblasts. These two homeodomain proteins can functionally interact to regulate the osteocalcin promoter. Perhaps most diagnostic of the osteoblast is the expression of osteocalcin, a non-collagenous matrix protein primarily produced by the osteoblast itself. This protein is integral to the bone regulating function of the osteoblast. Osteocalcin is essentially a small calcium binding protein expressed in bones and teeth undergoing mineralization.

As used herein, the term "osteopontin" refers to a form of osteopontin or a fragment thereof capable of influencing early bone matrix organization and mineralization through osteoblast or osteoclast cell attachment.

As used herein, the term "osteonectin" refers to a non-collagenous, calcium-binding glycoprotein of developing bone. It links collagen to mineral in the bone matrix.

It is further noted that a single marker for MSC status has not been identified, and likewise none of the markers described above are definitive for this cell type since their expression is somewhat broad, and can be found in less committed progenitors as well as more differentiated cells. This is perhaps indicative of the nature of an MSC. However, several definitive markers of the ES cells have been identified, which therefore enable one to assess progression away from the stem cells with pluripotent differentiation capacity. Undifferentiated hES cells also typically express Oct-4 and TERT, as detected by RT-PCR. Furthermore, under the microscope, ES cells appear to have high nuclear/cytoplasmic ratios, prominent nucleoli, and compact colony formation with poorly discernable cell junctions. Primate ES cells may express one or more of the stage-specific embryonic antigens (SSEA) 3 and 4, and markers detectable using antibodies designated Tra-1-60 and Tra-1-81 (Thomson et al., (1998) *Science* 282: 1145). Differentiation of hES cells in vitro typically results in the loss of these markers (if present) and increased expression of SSEA-1.

In order to monitor the expansion and differentiation of the ES cells at various stages of development experiments were conducted to test for the expression of a variety of gene markers. Thus, in accordance with the invention, FIG. 1 shows analysis of gene-specific markers in hES cells, EBs and cultured MSCs. In this experiment a variety of gene markers (i.e., Oct4, Cbfa1, ON, BMP2, BMP7, D1x5, Msx2, CMP and BSP) was tested. As anticipated, a dramatic reduction is observed in the expression of the ES cell markers Oct4 and BMP7 in EBs and MSCs 1 and 2. Also, enhanced expression of the matrix protein osteonectin (ON), and the osteoblast-specific differentiation factors Cbfa1, Msx2 and D1x5 in MSCs 2 population is observed. D1x5 is known to be expressed only in the most mature MSCs and pre-osteoblasts. These data are indicative of progression towards the osteoblast phenotype.

Figure 2:
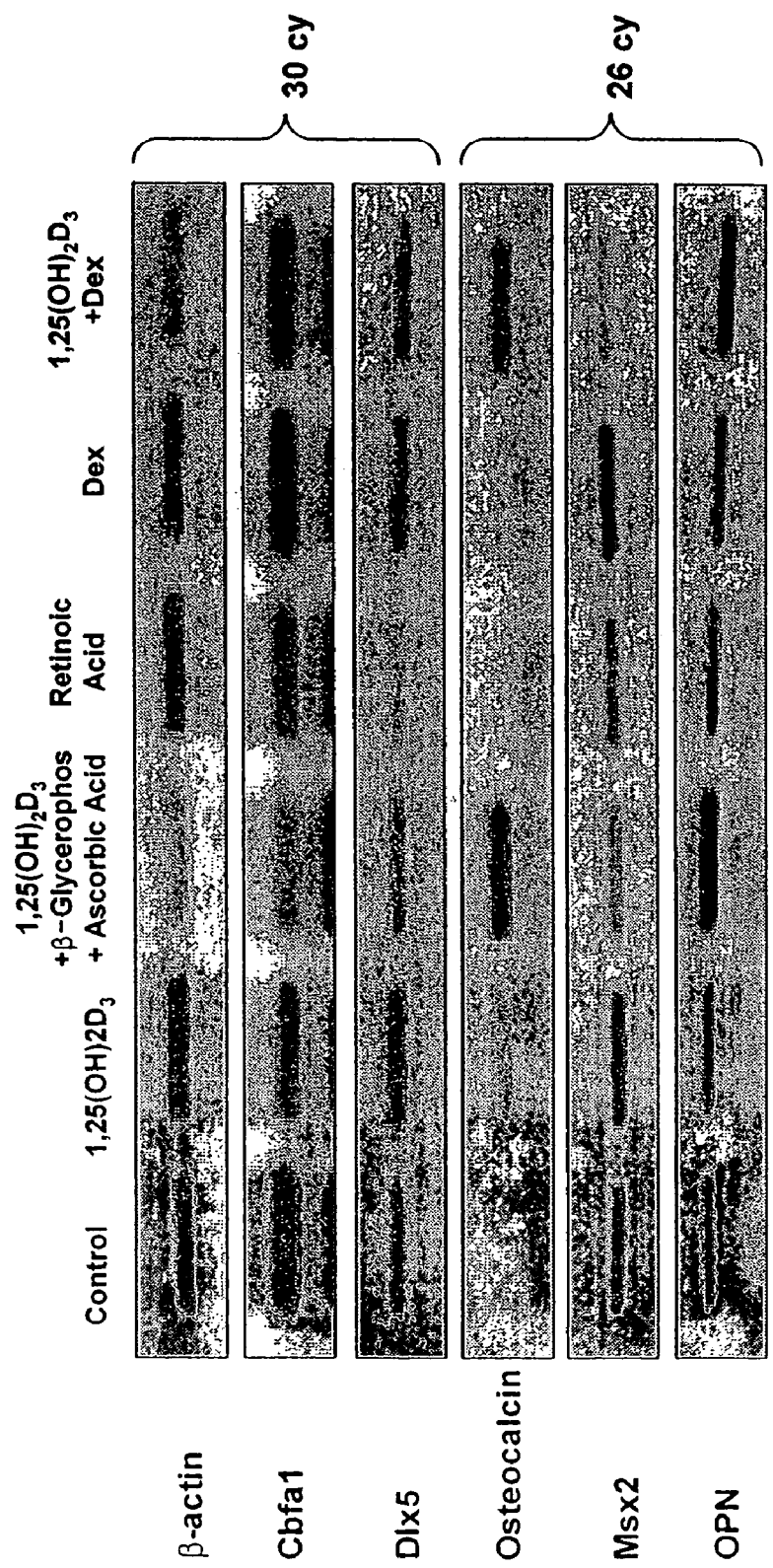
FIG. 2 depicts another RT-PCR analysis showing gene expression in osteoblasts derived from hES cells cultured in the presence of osteoblast differentiation agents.

One method used to characterize the osteoblast phenotype of the invention was by expression of gene markers, such as Cbfa-1, Msx2, D1x5, osteopontin (OPN), osteonectin, and osteocalcin at the mRNA and protein levels. These osteoblast-related gene markers range in function, but are generally involved in transcriptional regulation of bone-specific proteins and influencing earlier bone matrix organization and mineralization. As shown in FIG. 2, it appears that only 1.25 (OH)$_2$D$_3$ seems to be essential at inducing and regulating osteocalcin expression. Accordingly, the presence of the hormone is critical to the appearance of the mRNA for this protein. All of these data strongly support the authenticity of these hES-derived cells as osteoblasts. It is of interest to note that many factors such as retinoic acid or dexamethasone that are commonly known to act as osteoblast differentiation factors in mouse ES cells or bone marrow-derived mouse and human mesenchymal stem cells were unable to induce the expression of osteocalcin (hallmark gene for osteoblast differentiation) in the hES cells.

Figure 3:
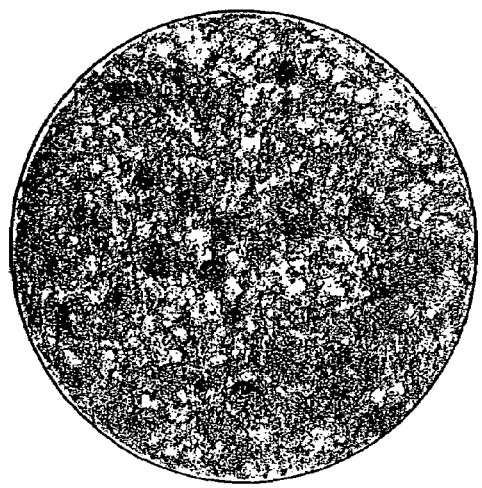
FIG. 3 shows osteoblasts derived from hES cells in culture stained using the Von Kossa technique to reveal bone nodule formation characterized by calcium phosphate co-precipitation.
Figure 3:
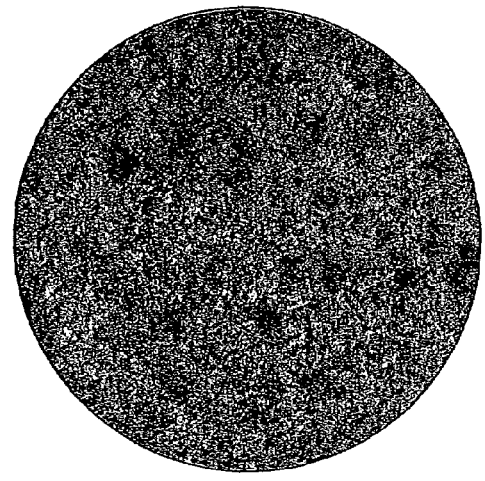
Figure 4:
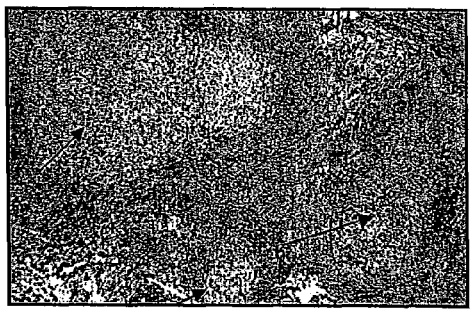
FIGS. 4A-D show photographs illustrating histological evaluation of nodules generated in nude mice: (A) shows large areas of cartilaginous nodules (4X); (B) shows evidence of endochondral bone formation (10X); (C) shows hypertrophic chondrocytes embedded in bone (20X); and (D) shows cartilage with hypertrophic chondrocytes and matrix (40X).
Figure 4:
Figure 4:
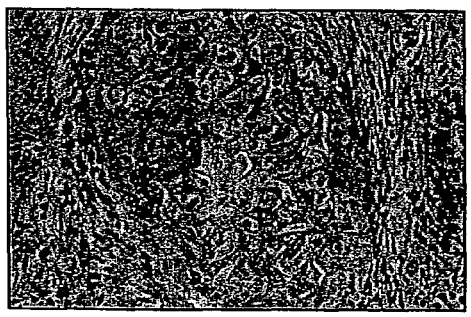
Figure 4:
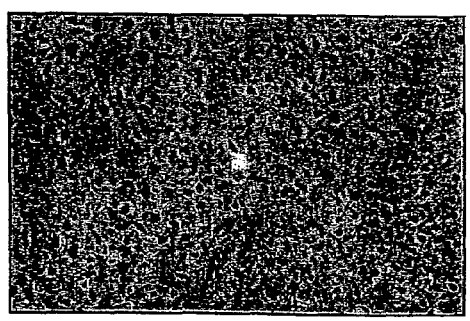
Figure 5:
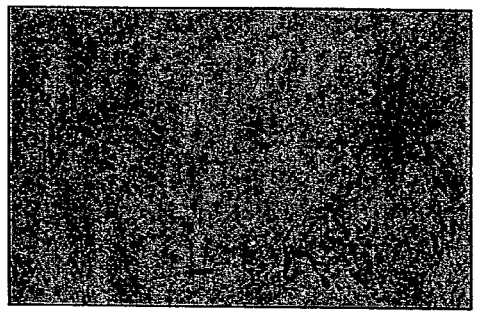
FIGS. 5A-D show photographs illustrating in vitro bone nodule formation with $1.25(OH)_2D_3$ treated MSCs: (A) shows control; (B) shows BMP2 treated cells; (C) shows $1.25(OH)_2D_3$ treated cells; and (D) shows BMP2 and $1.25(OH)_2D_3$ treated cells.
Figure 5:
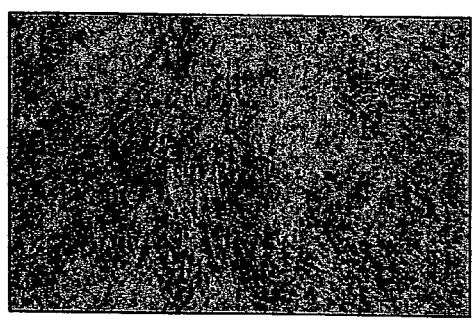
Figure 5:
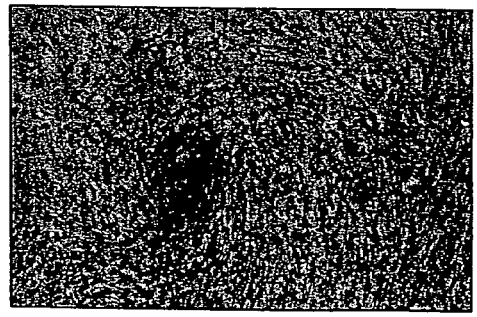
Figure 5:
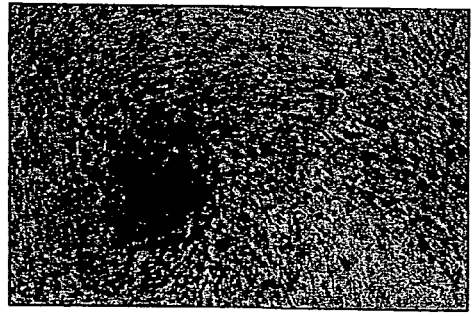

Another method used to characterize the osteoblast phenotype is the standard Von Kossa staining technique (Shevde, et al., (2001) *Cleft Palate Craniofac J*. 38:606-14). This staining technique was used to assess the ability of MSCs to form bone nodules. FIG. 3 shows in vitro bone nodule formation in osteoblasts derived from hES cells. Briefly, the cells were washed and stained for the presence of calcium phosphate deposits using the Von Kossa procedure. The number of calcified areas formed was then taken as an indication of the presence of osteoblast colonies. In addition to the in vitro bone nodule formation, applicants also envision that these bone precursor cells can be introduced into animals such as mice and primates to promote in vivo bone formation.

Yet another definitive osteoblast lineage restricted assay which can be used in practicing the invention includes the colony forming unit fibroblast (CFU-F) assay. This is a well-established method for the quantification of MSCs.

In Vivo Differentiation of hES Cell-Derived Mesenchymal Stem Cells

Mesenchymal stem cells were cultured according to the above-described protocol using Mesencult medium and pre-selected serum that support mesenchymal stem cell growth. To expand the population of MSCs, the cells were cultured in 10 cm dishes. A minimum of twenty-five dishes were required for one in vivo experiment. Also complete medium change was done one day prior to harvesting the cells (i.e., bone precursor cells).

Cells from all of the culture dishes were trypsinized, harvested and counted using the hemocytometer. After counting, cells were washed one time with PBS and resuspended in 100 ul of PBS for each spot injection. In general approximately $1.62 \times 10^6$ cells/200 ul were used for each injection. The cell suspension was then mixed with 100 ul of Matrigel™ (BD Biosciences) and kept on ice until the time of injection.

Figure 6:
FIG. 6 shows photographs of nude mice in the first week after subcutaneous injection of MSCs. The top panel in FIG. 6 represents mice from the control group and the bottom panel shows mice in the experimental group.
Figure 6:
Figure 7:
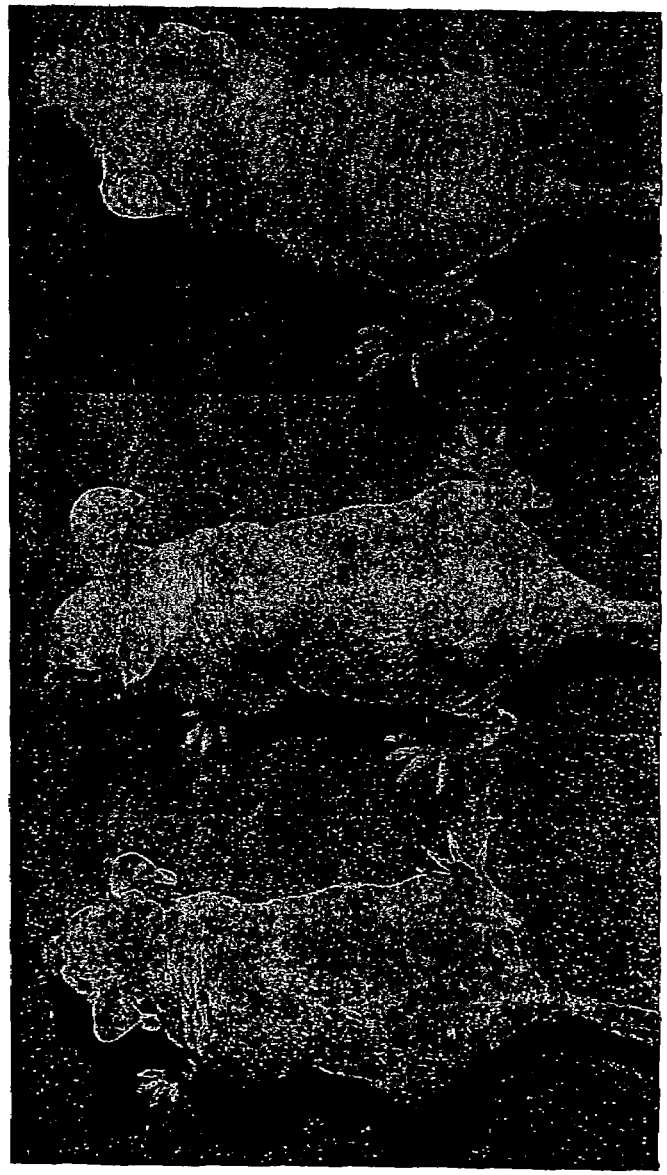
FIG. 7 shows photographs illustrating the progression of nodule growth in the nude mice from week 1 to week 8. There was no discomfort, pain or weight loss observed during the period of nodule growth.

Athymic nude mice (females, Harlan) of four to five weeks age were used for the in vivo experiments. The mice were divided into control and experimental groups. The cell suspension (200 ul) in Matrigel™ was injected subcutaneously into two separate locations on the dorsal surface (back) of the mice. Similarly, the control mice were injected with the same number of hES cells in Matrigel™. The mice were observed daily for any undesirable/unexpected changes, such as weight loss, inability to move, ulceration at the site of injection, etc. Also, photographs of the mice were taken at regular intervals and nodule growth was monitored closely. FIGS. 6 and 7 are the photographs taken of these mice.

Once the nodules reached the intended dimensions the mice were euthanized and the nodules were removed. The nodules were then cut in half and fixed in 10% buffered formalin. Histological sections (4-6 microns) were made and stained using Hematoxylin and Eosin to determine the presence of cartilage and bone in the nodules.

Histological evaluation of serial sections of subcutaneous bony nodules demonstrated large cartilaginous areas encapsulated by fibrous connective tissue. Several of the cartilaginous areas show evidence of bone formation as seen by the presence of mineralized matrix within the hypertrophic chondrocytes which is characteristic of endochondral bone formation. The sections also showed the presence of micro capillaries which is indicative of a successful vascularization process within the nodule. The results of the in vivo experiments show that mesenchymal stem cells and pre-osteoblasts derived from human ES cells have osteogenic potential and are able to form bone both in vitro and in vivo.

In yet another embodiment, it is envisioned that the cells described above can be implanted subcutaneously within an osteoconductive micro-crystalline scaffold environment. In this method, mesenchymal stem cells or pre-osteoblasts from the above procedures are seeded into sterile pre-wetted porous scaffolds (1.5 to $2.0 \times 10^{-6}$ cells per scaffold) in the appropriate medium and incubated for 12 hours to allow optimal cell attachment. Examples of suitable porous scaffolds include corraline hydroxyapatite and tricalcium phosphate cylindrical scaffolds (3 mm×2 mm; Berkeley Biomaterials). These seeded scaffolds are then implanted subcutaneously under the doral skin area of 4 to 5 week old athymic nude mice (two to four sites per mouse) and the mice observed daily for 4 weeks. Unseeded scaffolds can act as controls in such experiments. Following the 4 week period the mice would be subjected to a bone density analysis following which the mice would be sacrificed and the scaffolds removed. The scaffolds would not have bone nodules which could be fixed and analyzed. The osteoconductive environment will discourage the growth of other cell types both in the mesenchymal stem cell lineage as well as cells of other germ layers. This experiment is intended to demonstrate the sufficiency of human MSCs generated from human ES cells for ultimate use in human bone formation in vivo.

APPLICABILITY OF THE INVENTION

Human mesenchymal stem cells (MSCs) with the potential to form bone are a valuable source of biological material applicable to a variety of medical and dental fields. For example, it is envisioned that the substantially homogenous cell population of the invention can be utilized to provide a reproducible and renewable source of human osteoblasts with therapeutic potential for skeletal tissue regeneration or repair. It is encompassed that these cells can be used in tissue engineering to promote new bone growth, to enhance and accelerate the healing of fractures, to facilitate bone transplantation, and to secure and consolidate both dental as well as skeletal prosthetic devices. MSCs also offer a potential method for the targeted delivery of recombinant genes for gene therapy. Thus, these cell populations can be used for a number of important research, development, and commercial purposes.

Furthermore, the cells of this invention can be used to prepare a cDNA library relatively uncontaminated with cDNA preferentially expressed in cells from other progenitor cells, or end-stage cells from the osteoblast or any other developmental pathway.

The differentiated cells of this invention can also be used to prepare antibodies that are specific for markers of mesenchymal cells, osteoblasts, and intermediate precursors. Polyclonal antibodies can be prepared by injecting a vertebrate animal with cells of this invention in an immunogenic form. Production of monoclonal antibodies is described in such standard references as U.S. Pat. Nos. 4,491,632, 4,472,500 and 4,444,887, and *Methods in Enzymology* 73B:3 (1981). Specific antibody molecules can also be produced by contacting a library of immunocompetent cells or viral particles with the target antigen, and growing out positively selected clones. See Marks et al., (1996) *New Eng. J. Med.* 335:730, and McGuiness et al., (1996) *Nature* Biotechnol. 14:1449. A further alternative is reassembly of random DNA fragments into antibody encoding regions, as described in EP patent application 1,094,108 A.

It is further envisioned that other applications of this invention relate to using the substantially homogenous osteoblast population of the invention to facilitate screening of factors (such as solvents, small molecule drugs, peptides, oligonucleotides) or environmental conditions that affect the characteristics of such cells. For example, pharmaceutical compounds could be tested for their effect on musculoskeletal tissue maintenance or repair. In one illustration, the cell population of the invention maybe used to screen factors for their ability to affect calcium deposition. For example, one could screen a vitamin D library for compounds which have such an action on calcium deposition. Screening may be done either because the compound is designed to have a pharmacological effect on the cells, or because a compound designed to have effects elsewhere may have unintended side effects on cells of this tissue type. The screening can be conducted using any of the precursor cells or terminally differentiated cells of the invention.

Likewise, a variety of therapeutic uses are also envisioned for the substantially homogeneous osteoblast population of the invention, such as to enhance tissue maintenance or to repair the musculoskeletal system for any perceived need, such as an inborn error in metabolic function, the effect of a disease condition, or the result of significant trauma.

Although the foregoing invention has been described in some detail by way of illustration and example for purposes of clarity of understanding, it is understood that certain adaptations of the invention are a matter of routine optimization for those skilled in the art, and can be implemented without departing from the spirit of the invention, or the scope of the appended claims.

We claim:

1. A method of producing a population of human mesenchymal lineage cells comprising mesenchymal stem cells (MSCs) and bone precursor cells (BPCs) from human embryonic stem cells (hESCs), the method comprising the steps of:
    a) culturing hESCs under conditions conducive to form embryoid bodies (EBs);
    b) propagating the EBs formed in step a) in a mesenchyme-specific medium containing $1.25(OH)_2D_3$ to promote formation of EBs having cells of the mesenchymal lineage;
    c) digesting the resultant EBs of step b) and culturing the resulting cells in mesenchyme-specific medium to obtain a population of human mesenchymal lineage cells exhibiting spindle shaped morphology, wherein the population is composed of at least 60% human MSCs, and wherein the population exhibits enhanced expression of Cba-1, Msx2, and D1x5 relative to the EBs of step a); and
    d) propagating the human MSCs produced by step c).

2. The method of claim 1 further comprising the step of:
    e) culturing the human MSCs in the presence of an effective amount of $1.25(OH)_2D_3$, dexamethasone, retinoic acid, or a combination thereof to cause the MSCs to differentiate into a subpopulation of BPCs composed of at least 80% pre-osteoblast and osteoblast cells, wherein the BPCs are characterized by the expression of osteopontin, osteonectin, and, osteocalcin.

3. The method of claim 2 further comprising the step of:
    f) exposing the subpopulation of BPCs to an effective amount of ascorbic acid and β-glycerophosphate to further propagate and differentiate the BPCs into osteoblast cells capable of forming bone nodules.

4. The method of claim 1 wherein the population of human mesenchymal lineage cells includes at least 90% mesenchymal stem cells.

5. A method as claimed in claim 1 wherein the mesenchyme-specific medium further includes serum.

6. A method as claimed in claim 1 further comprising the step of culturing the population of MSCs in a medium having an effective amount of $1.25(OH)_2D_3$ to direct differentiation of MSCs into bone precursor cells capable of forming bone nodules.

7. A method as claimed in claim 1 wherein the time period to go from human embryonic stem cells to bone precursor is less than 34 days.

8. A method of producing a population of human bone-precursor cells (BPCs) from human embryonic stem cells (hESCs) comprising the steps of:
    a) culturing hESCs under conditions conducive to form embryoid bodies (EBs);
    b) culturing the EBs in a mesenchyme-specific medium containing $1,25(OH)_2D_3$ to form a population of mesenchymal lineage cells exhibiting spindle shaped morphology, wherein the population is composed of at least 60% human mesenchymal stem cells (MSCs), and wherein the population exhibits enhanced expression of Cba-1, Msx2, and D1x5 relative to the EBs of step a); and
    c) culturing the population of MSCs in an effective amount of $1,25(OH)_2D_3$, dexamethosone, retinoic acid, or a combination thereof to induce the MSCs to differentiate into a subpopulation of BPCs composed of at least 80% pre-osteoblast and osteoblast cells, wherein the BPCs are characterized by the expression of osteopontin, osteonectin, and osteocalcin.

9. A method of directing the differentiation of human embryonic stem cells (hESCs) into cells of the mesenchymal lineage comprising the steps of:
    a) culturing the hESCs under conditions conducive to form embryoid bodies (EBs);
    b) propagating the EBs formed in step a) in a mesenchyme-specific medium containing $1,25(OH)_2D_3$ to promote formation of EBs having cells of the mesenchymal lineage;
    c) digesting the resultant EBs of step b) and culturing the resulting cells in mesenchyme-specific medium to obtain a population of human mesenchymal lineage cells exhibiting spindle shaped morphology, wherein the population is composed of at least 60% human MSCs, and wherein the population exhibits enhances expression of Cba-1, Msx2, and D1x5 relative to the EBs of step a).

* * * * *

UNITED STATES PATENT AND TRADEMARK OFFICE
CERTIFICATE OF CORRECTION

| | |
|---|---|
| PATENT NO. | : 7,592,176 B2 |
| APPLICATION NO. | : 11/123794 |
| DATED | : September 22, 2009 |
| INVENTOR(S) | : J. Wesley Pike et al. |

It is certified that error appears in the above-identified patent and that said Letters Patent is hereby corrected as shown below:

Column 1, line 15 should read:

--STATEMENT REGARDING FEDERALLY SPONSORED RESEARCH OR DEVELOPMENT

This invention was made with United States government support awarded by the following agency:

NIH AR45173

The United States government has certain rights in this invention.--.

Column 3, line 17, the word "1.25(OH)2D3" should be --1,25(OH)2D3--.

Column 3, line 22, the word "1.25(OH)2D3" should be --1,25(OH)2D3--.

Column 3, line 35, the word "1.25(OH)2D3" should be --1,25(OH)2D3--.

Column 4, line 13, the word "1.25(OH)2D3" should be --1,25(OH)2D3--.

Column 4, line 15, the word "1.25(OH)2D3", which appears twice in this line, should be --1,25(OH)2D3--.

Column 4, line 48, the word "1.25(OH)2D3" should be --1,25(OH)2D3--.

Column 4, line 54, the word "1.25(OH)2D3" should be --1,25(OH)2D3--.

Column 4, line 56, the word "1.25(OH)2D3" should be --1,25(OH)2D3--.

Column 5, line 14, the word "1.25(OH)2D3" should be --1,25(OH)2D3--.

Column 5, line 33, the word "1.25(OH)2D3" should be --1,25(OH)2D3--.

Column 7, line 21, the word "1.25(OH)2D3" should be --1,25(OH)2D3--.

Column 7, line 27, the word "1.25(OH)2D3" should be --1,25(OH)2D3--.

Column 7, line 33, the word "1.25(OH)2D3" should be --1,25(OH)2D3--.

UNITED STATES PATENT AND TRADEMARK OFFICE
CERTIFICATE OF CORRECTION

PATENT NO. : 7,592,176 B2
APPLICATION NO. : 11/123794
DATED : September 22, 2009
INVENTOR(S) : J. Wesley Pike et al.

It is certified that error appears in the above-identified patent and that said Letters Patent is hereby corrected as shown below:

Column 11, line 37, the word "1.25(OH)2D3" should be --1,25(OH)2D3--.

Column 11, line 49, the word "1.25(OH)2D3" should be --1,25(OH)2D3--.

Column 12, line 1, the word "1.25(OH)2D3" should be --1,25(OH)2D3--.

Column 12, line 3, the word "1.25(OH)2D3" should be --1,25(OH)2D3--.

Column 12, line 44, the word "1.25(OH)2D3" should be --1,25(OH)2D3--.

Column 12, line 46, the word "1.25(OH)2D3" should be --1,25(OH)2D3--.

Column 12, line 48, the word "1.25(OH)2D3" should be --1,25(OH)2D3--.

Column 12, line 50, the word "1.25(OH)2D3" should be --1,25(OH)2D3--.

Column 12, line 51, the word "1.25(OH)2D3" should be --1,25(OH)2D3--.

Column 12, line 64, the word "1.25(OH)2D3" should be --1,25(OH)2D3--.

Column 12, line 67, the word "1.25(OH)2D3" should be --1,25(OH)2D3--.

Column 13, line 5, the word "1.25(OH)2D3" should be --1,25(OH)2D3--.

Column 13, line 39, the word "1.25(OH)2D3" should be --1,25(OH)2D3--.

Column 14, line 47, the word "1.25(OH)2D3" should be --1,25(OH)2D3--.

Column 17, line 26, Claim 1(b), the word "1.25(OH)2D3" should be --1,25(OH)2D3--.

Column 17, line 40, Claim 2(e), the word "1.25(OH)2D3" should be --1,25(OH)2D3--.

Column 17, line 40, Claim 2(e), the word "or" is omitted; line 40 should be --"amount of 1,25(OH)2D3, or dexamethasone, or retinoic"--.

UNITED STATES PATENT AND TRADEMARK OFFICE
CERTIFICATE OF CORRECTION

PATENT NO.       : 7,592,176 B2
APPLICATION NO.  : 11/123794
DATED            : September 22, 2009
INVENTOR(S)      : J. Wesley Pike et al.

It is certified that error appears in the above-identified patent and that said Letters Patent is hereby corrected as shown below:

Column 18, line 8, Claim 6, the word "1.25(OH)2D3" should be --1,25(OH)2D3--.

Column 18, line 12, Claim 7, the word "cells" is omitted; line 12 should be --"to go from human embryonic stem cells to bone precursor cells is"--.

Signed and Sealed this

First Day of December, 2009

David J. Kappos
*Director of the United States Patent and Trademark Office*